United States Patent [19]
Brox

[11] Patent Number: 4,888,239
[45] Date of Patent: Dec. 19, 1989

[54] ETHANOL FILL FORMULATION FOR SOFGELS ETC.

[75] Inventor: Werner Brox, Beerfelden, Fed. Rep. of Germany

[73] Assignee: R. P. Scherer Corporation, Troy, Mich.

[21] Appl. No.: 89,065

[22] Filed: Aug. 25, 1987

[30] Foreign Application Priority Data

Aug. 28, 1986 [DE] Fed. Rep. of Germany ....... 3629386

[51] Int. Cl.$^4$ ............................................... B32B 5/16
[52] U.S. Cl. .................................................. 428/402.2
[58] Field of Search ........................... 428/320.2, 402.2

[56] References Cited

U.S. PATENT DOCUMENTS

| | | | |
|---|---|---|---|
| 4,029,758 | 6/1977 | Mlodozeniec et al. | 428/192 X |
| 4,062,799 | 12/1977 | Matsukawa et al. | 428/402.2 X |
| 4,627,850 | 12/1986 | Deters et al. | 428/308.4 X |
| 4,717,566 | 1/1988 | Eckenhoff et al. | 514/53 X |
| 4,717,568 | 1/1988 | Eckenhoff et al. | 428/320.2 X |

Primary Examiner—Peter A. Nelson
Attorney, Agent, or Firm—Allegretti & Witcoff, Ltd.

[57] ABSTRACT

Gelatin capsules of the type having an outer shell comprising gelatin and, optionally, a plasticizer, and a capsule filling, the filling containing at least one active substance and/or a dietetic agent or foodstuff as well as a solvent mixture, the solvent mixture containing about 5–50% by weight, preferably 10–30% by weight of ethanol and about 20–95% by weight, preferably 40–90% by weight of one or more of partial glycerides of fatty acids havig from 6 to 18 carbon atoms. The capsules are prepared by dissolving the active ingredients in the solvent mixture and filling the resulting mixture into the gelatin capsules.

20 Claims, No Drawings

ETHANOL FILL FORMULATION FOR SOFGELS ETC.

BACKGROUND OF THE INVENTION

The present invention relates to gelatin capsules, both hard shell and soft shell or softgels, consisting of an envelope or shell comprising gelatin and optionally a plasticizer and a capsule filling containing at least one active substance and/or a dietetic agent or foodstuff as well as a solvent mixture, and to a process for preparing such capsules or softgels.

Soft gelatin capsules or softgels are predominantly used to contain liquids wherein the active ingredients are present in the dissolved or suspended state. The employed filling materials commonly include vegetable oils, animal oils and mineral oils, liquid hydrocarbons, ethereal oils and polyethylene glycol. Fats and waxes are also commonly used or added to the fill for increasing the consistency.

In recent years, there have also been developed processes for filling liquids and pasty filling materials into two piece, telescoping hard gelatin capsules.

A particularly good bioavailability of pharmacologically active substances in the fill of the gelatin capsules is attained if the active substance is successfully dissolved in a suitable solvent and the encapsulated solution is administered to a patient. However, such solvents may only include adjuvants which, on the one hand, are acceptable for application to the human organism and, on the other hand, do not impair the stability of the gelatin shell or envelope.

As discussed in DE-OS 33 07 353, there are known soft gelatin capsules or softgels containing, as a solvent, polyethylene glycol having an average molecular weight of 600 as well as glycerol and/or 1,2-propylene glycol. These soft gelatin capsules have proven to be very valuable. However, such polyethylene glycols are considered to be unsuitable solvents for some active substances. There are sensitive action materials such as, for example, sulfonamides or organic iodine compounds which are chemically instable in polyethylene glycols. Furthermore, a number of active substances have been known, for example, phenols or phenobarbital, for which a complex formation occurs between the ethoxyl groups of the polyethylene glycols and the active substances, which complexes cause a reduced bioavailability of the active substances to result. Eventually, there are also higherdosed active materials, for example pentetrazole, which are not sufficiently soluble in polyethylene glycols.

SUMMARY OF THE INVENTION

Thus, it is an object of the present invention to find solvents which are allowed for human applications, which have good solvent power, and which do not produce undesired complexes by ethoxyl groups.

Ethanol has been known as being a good solvent for many pharmaceutically active substances and is frequently used for the preparation of dropping solutions. Contrary thereto, ethanol, thus far, could not be used for individual-dose gelatin capsules of sufficiently high concentration, since concentrated ethanol is absorbed by the gelatin shell or envelope of the capsule, after preparation, and the gelatin shell becomes softened and deformed thereby; as a result, the capsules with the deformed gelatin shells are not acceptable in the trade.

According to what has been set forth by Czetsch-Lindenwald and Fahrig, Arzneikapseln Aulendorf, 1962, p. 34, lower aliphatic alcohols may be filled into capsules only to about 5% by weight. In admixture with polyethylene glycols, in a specific recipe, according to DE-OS 35 09 741, a maximum of 10% ethanol may be filled into gelatin capsules. However, the example therein only contains 7% by weight of ethanol. This is confirmed by the European Patent Publication 0 170 623 which employs ethanol as a solvent for the active substance dihydro-(val)$^2$-cyclosporine. Drink solutions contain 10 to 12% by weight of ethanol, whereas the soft gelatin capsules according to Example 2 contain only from 2 to 5% by weight.

It has now surprisingly found that ethanol mixtures having an ethanol content in excess of 5% by weight, up to about 50% by weight, can also be encapsulated without the addition of ethylene glycols to form stable preparations, if the solvent mixture contains at least 20%, up to about 95% by weight of partial glycerides of fatty acids having from 6 to 18 carbon atoms. A preferred range of ethanol is about 10-30% by weight and a preferred range of the partial glycerides of fatty acids is 40-90% by weight. Partial glycerides of fatty acids having from 6 to 12 carbon atoms and/or ricinoleic acid are preferred to be employed.

DETAILED DESCRIPTION OF THE PREFERRED EMBODIMENT

The gelatin capsules which are the subject of the present invention comprise a gelatin shell which encloses a filling including an active substance, a dietetic agent or a foodstuff and a solvent mixture, the solvent mixture containing about 5–50% (preferably 10–30% by weight) by weight of ethanol and about 20–95% by weight (preferably 40–90% by weight) of one or more partial glycerides of fatty acids having from 6–18 carbon atoms. The partial glycerides useful in the fill include monoglycerides or diglycerides as well as mixtures thereof. Suitable commercially available products include, for example, glycerol monocaprylate (Imwitor 308 of Dynamit Nobel), glycerol monodicaprylate (Imwitor 908), mixtures comprising glycerol monodicaprylate and glycerol monodicaprate (Imwitor 742) and partial glycerides of ricinoleic acid (Softigen 701 and Rilanit).

These partial glycerides are readily miscible with ethanol and even allow amounts of ethanol in excess of 10% to be employed in the solvent mixture without any deterioration of the stability of the gelatin envelope.

The gelatin capsules according to the present invention are prepared by dissolving the active substance in the mixture of ethanol and partial glycerides. As the ethanol-partial glyceride mixtures are miscible and lipophilic as well as hydrophilic components, various additives may be used if required, e.g. triglycerides of various fatty acids or polyethylene glycols, provided that they do not impair the stability of the active substances or of the gelatin shell of the capsule.

The solutions according to the invention may be filled into hard gelatin capsules as well as into soft gelatin capsules. The envelope of soft gelatin capsules usually contains one or more plasticizers in addition to gelatin, such as glycerol, propylene glycol. sorbitol, or sorbitans. The shell may also contain colorants, preservatives, flavoring agents, sugar and other polyols.

When using soft gelatin capsules or softgels, the capsules are simultaneously formed and filled with a fill material using conventional methods and procedures such as the rotary die process as discussed, for example, in the article of J.P. Stanley, "II. Soft Gelatin Capsules," pp. 360–384, *The Theory and Practice of Industrial Pharmacy*. Soft gel capsules or softgels conventionally comprise gelatin, a plasticizer, such as glycerin, or sorbitol and water. The gelatin shells also commonly contain a preservative, such as mixed parabens, for example, methyl or propyl parabens. The parabens are incorporated into the shell formulation in minor proportions as compared to the total weight of the shell formulation. Conventional soft gelatin capsules utilize gelatin having a bloom value of 150 to 200 although this value may be varied. The fill material can vary over a wide range and may contain unit dosage amounts of pharmaceuticals, dietary supplements, vitamins and the like, often in liquid form. The capsules are commonly sized and shaped so as to be readily swallowable by a person, usually with the aid of water.

The invention is further illustrated by way of the following examples.

EXAMPLE 1

A mixture of 300 mg of glycerol monocaprylate (Imwitor 308) and 150 mg of ethanol was filled into soft gelatin capsules in a known manner according to the Rotary Die Process, and the capsules were dried. Then the ethanol content of the capsule envelope was analyzed, and an ethanol content of 4.5% was found. The capsules were physically stable; capsule shape and capsule hardness were excellent.

COMPARATIVE EXAMPLE 1

400 mg of ethanol were filled into soft gelatin capsules as in Example 1. After drying the ethanol content of the capsule envelope was 14.0%. The capsules were physically instable, deformed and shrinked due to the ethanol loss.

COMPARATIVE EXAMPLE 2

The mixture of 350 mg of medium-chain triglycerides (Miglyol 812) and 100 mg of ethanol were filled into soft gelatin capsules as in Example 1. After drying the ethanol content of the capsule envelope was 11.8%. The capsules were physically instable. They were soft and deformed.

EXAMPLE 2

A mixture of 300 mg of glycerol mono/dioleate and 150 mg of ethanol were filled into soft gelatin capsules as in Example 1. After drying the ethanol content of the capsule envelope was 7.8%. The capsule shape was satisfactory, but the capsules were softer than those of Example 1 because of the higher ethanol content in the envelope.

EXAMPLE 3

Hard gelatin capsules of size O having an average weight of 97 mg were filled with a mixture of 80% of glycerol monocaprylate (Imwitor 308) and 20% of ethanol and sealed with a gelatin filament. After one week the ethanol content of the capsule envelope was analyzed. The capsule envelopes contained 2% of ethanol, based on 97 mg of capsule envelope.

COMPARATIVE EXAMPLE 3

Hard gelatin capsules of size O as in Example 3 were filled with a mixture of 80% of medium-chain triglycerides (Miglyol 812) and 20% of ethanol and sealed with a gelatin filament. After one week the ethanol content of the capsule envelope was 11.1%, based on 97 mg of capsule envelope.

| Pentetrazol | 100 mg |
| Ethanol | 20 mg |
| Imwitor 742 | 100 mg |
| Fill in weight | 220 mg |

Ethanol was added to the molten Imwitor 742, and the Pentetrazol was dissolved in the mixture. The finished solution was filled into soft gelatin capsules of size 4 minims. The dried capsules were unobjectionable with respect to capsule hardness and capsule appearance.

EXAMPLE 5

| Phenobarbital | 15.0 mg |
| Ethanol | 50 mg |
| Glycerol monoricinoleate (Softigen 701) | 150.0 mg |
| Fill-in weight | 215.0 mg |

Phenobarbital was dissolved in the mixture of ethanol and glycerol monoricinoleate and filled into soft gelatin capsules. the capsules were unobjectionable with respect to capsule hardness and capsule appearance.

While in the foregoing there has been provided a detailed description of preferred embodiments of the present invention, it is to be understood that all equivalents obvious to those of ordinary skill in the art are to be included within the scope of the invention as claimed.

What is claimed is:

1. A capsule having a gelatin shell and the filling therein, said filling comprising an active material and a solvent, said solvent consisting essentially of at least 5% by weight of ethanol and at least 20% by weigh of partial glycerides of fatty acids having from 6–18 carbon atoms.

2. The capsule of claim 1 wherein said active substance is a dietary substance.

3. The capsule of claim 1 wherein said active substance is a food supplement.

4. The capsule of claim 1 wherein said active substance is a pharmaceutical substance.

5. The capsule of claim 1 wherein said ethanol is present in an amount of about 5–50% by weight and said partial glycerides of fatty acids are present in an amount of about 20–95% by weight.

6. The capsule of claim 1 wherein said ethanol is present in an amount of about 10–30% by weight and said partial glycerides of fatty acids are present in an amount of about 40–95% by weight.

7. The capsule of claim 1 wherein said partial glycerides of fatty acids have from 6–12 carbon atoms.

8. The capsule of claim 1 wherein said partial glycerides of fatty acids is ricinoleate acid.

9. A process for preparing a gelatin capsule of the type having a gelatin shell and a fill material enclosed within said gelatin shell, said process comprising the steps of dissolving an active substance in a solvent, said solvent consisting essentially of at least 5% by weight of ethanol and at least 20% by weight of partial glycerides of fatty acids having from 6-18 carbon atoms, and filling the solution into the gelatin capsule.

10. The process of claim 9 wherein said active substance is a dietary substance.

11. The process of claim 9 wherein said active substance is a food supplement.

12. The process of claim 9 wherein said active substance is a pharmaceutical substance.

13. The process of claim 9 wherein said ethanol is present in an amount of about 5-50% by weight and said partial glycerides of fatty acids are present in an amount of about 20-95% by weight.

14. The process of claim 9 wherein said ethanol is present in an amount of about 10-30% by weight and said partial glycerides of fatty acids are present in an amount of about 40-90% by weight.

15. The process of claim 9 wherein said partial glycerides of fatty acids have from 6-12 carbon atoms.

16. The process of claim 9 wherein said partial glycerides of fatty acids is ricinoleate acid.

17. The capsule of claim 1 wherein said solvent additionally includes a fatty acid triglyceride.

18. The capsule of claim 1 wherein said solvent additionally includes a polyethylene glycol.

19. The process of claim 9 wherein said solvent additionally includes a fatty acid triglyceride.

20. The process of claim 9 wherein said solvent additionally includes a polyethylene glycol.

* * * * *